United States Patent
Gutierrez

(10) Patent No.: US 7,181,260 B2
(45) Date of Patent: Feb. 20, 2007

(54) APPARATUS AND METHOD FOR MEASURING MYOCARDIAL OXYGEN CONSUMPTION

(76) Inventor: Guillermo Gutierrez, 6791 Father John Ct., McLean, VA (US) 22101

( * ) Notice: Subject to any disclaimer, the term of this patent is extended or adjusted under 35 U.S.C. 154(b) by 265 days.

(21) Appl. No.: 10/987,505

(22) Filed: Nov. 12, 2004

(65) Prior Publication Data
US 2005/0124872 A1 Jun. 9, 2005

Related U.S. Application Data

(60) Provisional application No. 60/520,280, filed on Nov. 14, 2003.

(51) Int. Cl.
*A61B 5/00* (2006.01)
(52) U.S. Cl. ......... 600/325; 600/323; 600/324
(58) Field of Classification Search .......... 600/323, 600/324, 325, 339, 340, 341, 342
See application file for complete search history.

(56) References Cited

U.S. PATENT DOCUMENTS

| | | | | |
|---|---|---|---|---|
| 3,995,623 A | * | 12/1976 | Blake et al. | 600/381 |
| 4,684,245 A | * | 8/1987 | Goldring | 356/41 |
| 5,435,308 A | * | 7/1995 | Gallup et al. | 600/342 |
| 5,788,647 A | * | 8/1998 | Eggers | 600/526 |
| 6,299,583 B1 | * | 10/2001 | Eggers et al. | 600/526 |
| 6,532,378 B2 | * | 3/2003 | Saksena et al. | 600/381 |
| 7,010,337 B2 | * | 3/2006 | Furnary et al. | 600/325 |

OTHER PUBLICATIONS

Lakhmir S. Chawla, MD, et al., "Lack of Equivalence Between Central and Mixed Venous Oxygen Saturation" Dec. 6, 2004, pp. 1891-1896, Chest 126.

Konrad Reinhart, et al., "Continous central venous and pulmonary artery oxygen saturation monitoring in the critically ill" Intensive Care Med (2004) 30: pp. 1572-1578

Emanuel Rivers, MD,MPH., et al., "Early Goal-Directed Therapy in the Treatment of Severe Sepsis and Septic Shock" Nov. 8, 2001, pp. 1368-1377, N Engl J Med, vol. 345, No. 19.

Michael D. Crittenden, MD, "Intraoperative Metabolic Monitoring of the Heart: I. Clinical Assessment of Coronary Sinus Metabolites", 2001; 72:S2220-6, The Society of Thoracic Surgeons Published by Elsevier Science Inc.

Darrel P. Francis, MA, MRCP, et al., "Oxygenation in Patients with a Functionality Univentricular Circulation and complete Mixing of Blood" 1999 pp. 2198-2203, American Heart Association, Inc.

Gordon R. Bernard, MD, et al., "Pulmonary Artery Catheterization and Clinical Outcomes", May 17, 2000, pp. 2559-2577, JAMA, vol. 283, No. 19.

* cited by examiner

*Primary Examiner*—Eric F. Winakur
*Assistant Examiner*—Jack Lin
(74) *Attorney, Agent, or Firm*—Holland & Knight LLP; John P. Moran

(57) ABSTRACT

Disclosed is a pulmonary artery catheter ("PAC") that is used in determining myocardial oxygen consumption. Myocardial oxygen consumption is of critical importance because decreased myocardial energy utilization during acute illness may lead to tissue hypoperfusion, multiple organ failure, and eventually death. The inventor has discovered that myocardial oxygen consumption is a function of the difference in oxygen levels in atrial and mixed venous blood. The invention has further discovered that differences in lactate, glucose or any other measurable blood concentration metabolite in atrial or superior vena cava and mixed venous blood can also be used in determining myocardial oxygen consumption.

12 Claims, 3 Drawing Sheets

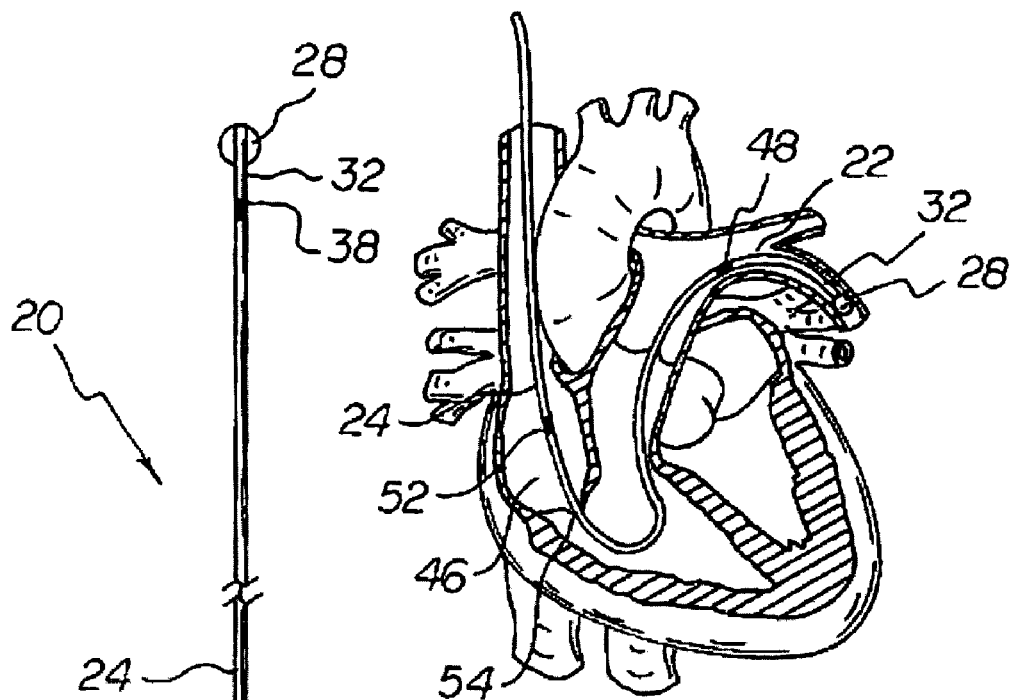
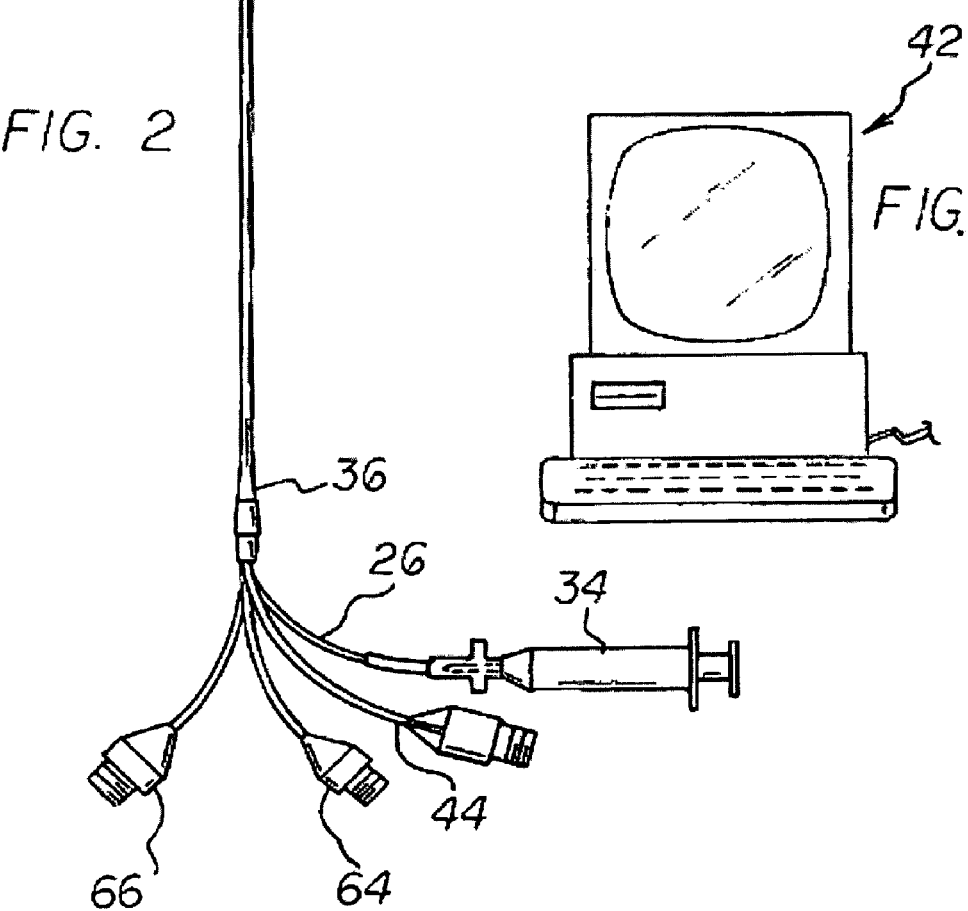

US 7,181,260 B2

APPARATUS AND METHOD FOR MEASURING MYOCARDIAL OXYGEN CONSUMPTION

RELATED APPLICATION DATA

This invention claims priority from provisional application Ser. No. 60/520,280 filed on Nov. 14, 2003 entitled Novel Method to Measure Myocardial Oxygen Consumption in Critically Ill Patients, the contents of which are incorporated herein by reference.

BACKGROUND OF THE INVENTION

1. Field of the Invention

This invention relates to an apparatus and method for measuring myocardial oxygen consumption. More particularly, the present invention relates to determining myocardial oxygen consumption by comparing oxygen saturation in atrial and mixed venous blood.

2. Description of the Background Art

Pulmonary artery catheters ("PACs") are widely used for patient diagnosis and for hemodynamic and therapeutic monitoring. One of the most widely used PACs is the Swan-Ganz catheter. The Swan-Ganz catheter, a version of which is disclosed in U.S. Pat. No. 3,995,623 to Blake, includes a flexible tube (enclosing multiple lumina) that is designed to be flow-directed through a patient's heart by a distal balloon. The catheter is adapted to be delivered through the right atrium and right ventricle with the distal end positioned within the pulmonary artery.

The Swan-Ganz catheter includes first and second lumina for use in measuring blood pressures in the pulmonary artery and right atrium respectively. A third lumen is used for inflating the balloon at the distal end of the catheter. A fourth lumen is included for housing a thermistor that is used in monitoring blood temperature and in determining cardiac output. The fourth lumen also houses the wires associated with electrodes that are included for monitoring intraatrial and intraventricular electrograms. The Swan-Ganz catheter has been a useful tool in diagnosing complex cardiac arrhythmias.

A more recent PAC construction is disclosed in U.S. Pat. No. 6,532,378 to Saksena. In one embodiment, the PAC of Saksena includes a series of defibrillation electrodes interspersed with mapping electrode pairs at the distal end of the catheter. Proximal to the defibrillation and mapping electrodes are a series of sense electrodes and additional defibrillation electrodes. The catheter is used for indirect left atrial mapping from the left pulmonary artery and is also used in defibrillating or cardioverting the heart.

Each of the above referenced inventions is useful in providing a physician with information on the mechanical functioning of a patient's heart. However, none of the aforementioned PACs can be used to measure the rate of oxygen consumption by the heart, or myocardial $VO_2$, whereby a physician may gain an understanding of the energy costs associated with the heart's performance. Measuring myocardial $VO_2$ is significant because a decrease in myocardial $VO_2$ may have serious consequences for critically ill patients. Heretofore, there has been no practical way to obtain myocardial $VO_2$ measurements in critically ill patients.

SUMMARY OF THE INVENTION

It is therefore one of the objectives of this invention to provide a pulmonary artery catheter that can be used in measuring the rate of oxygen consumption by the heart, or myocardial $VO_2$.

It is also an object of this invention to detect myocardial metabolism via the differential measurement of oxygen saturation in the atrial and mixed venous blood.

Another object of this invention is to measure atrial and mixed venous blood differences in lactate, glucose or any other measurable blood concentration metabolite to serve as a measure of myocardial metabolism.

Still another object of this invention is to provide a catheter which simultaneously measures oxygen levels in the pulmonary artery and the right atrium and on the basis of these measurements derives the rate of oxygen consumption by the heart.

These and other objects are achieved by providing a pulmonary artery catheter comprising an elongated flexible tube. The catheter includes a first oxygen sensor located adjacent the distal end of the tube for determining blood oxygen content. The first sensor is adapted to be positioned within a patient's pulmonary artery. A second oxygen sensor is positioned proximal to the first oxygen sensor and likewise determines blood oxygen content. The second oxygen sensor is adapted to be positioned within a patient's right atrium. Finally, a microprocessor is operatively coupled to the first and second oxygen sensors, with the microprocessor implementing an algorithm whereby the rate of oxygen consumption in the heart is calculated as a function of the difference between blood oxygen content as measured by the first and second oxygen sensors.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a partial cross sectional view of the catheter of the present invention positioned within the right atrium and pulmonary artery of a human heart.

FIG. 2 is a view of the catheter employed in carrying out the principles of the present invention.

FIG. 3 is a view of a computer for use in conjunction with the catheter of the present invention.

Similar reference characters refer to similar parts throughout the several views of the drawings.

DETAILED DESCRIPTION OF THE PREFERRED EMBODIMENT

Figure 4:
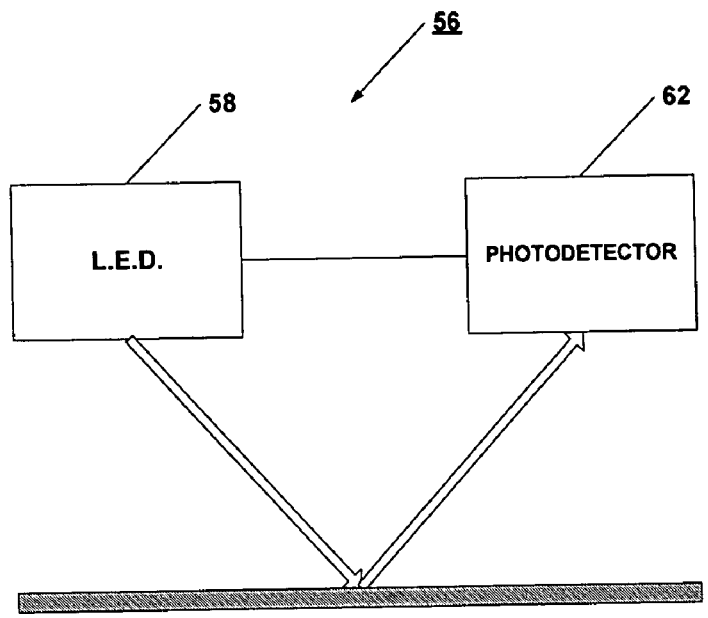
FIG. 4 is a block diagram illustrating one of the optical sensors of the present invention.

The present invention relates to a pulmonary artery catheter ("PAC") that is used in determining myocardial oxygen consumption. Myocardial oxygen consumption is of critical importance because decreased myocardial energy utilization during acute illness may lead to tissue hypoperfusion, multiple organ failure, and eventually death. The inventor has discovered that myocardial oxygen consumption is a function of the difference in oxygen levels in atrial (or central veins) and mixed venous blood. The inventor has further discovered that differences in lactate, glucose or any other measurable blood concentration metabolite in atrial or central venous blood and mixed venous blood can also be used in determining myocardial energy metabolism.

The measurements necessary to calculate myocardial oxygen consumption are carried out by way of a PAC. FIG. 1 illustrates PAC 20 positioned within the pulmonary artery 22 of a patient's heart. As is conventional, PAC 20 of the present invention is constructed from an elongated flexible tube 24. Tube 24, which may be coated with a material to facilitate its insertion into a patient's vein, houses a series of lumina each of which serves a different diagnostic or therapeutic purpose.

For example, one lumen 26 is used to selectively inflate or deflate a balloon 28 at the distal end 32 of PAC 20. Balloon 28 is preferably formed from a flexible material that expands upon receiving a fluid through lumen 26. This fluid can be selectively injected into or withdrawn from balloon 28 via a syringe 34 at the proximal end 36 of PAC 20. When inflated, balloon 28 allows PAC 20 to be "flow-directed" to a patient's heart.

PAC 20 additionally includes a thermistor 38 positioned adjacent to balloon 28. The use of thermistors in PACs is known in the art and is generally described in U.S. Pat. No. 3,995,623 to Blake. Electrical leads (not shown) are used to couple thermistor 38 to a microprocessor 42, or other diagnostic equipment, as will be described in greater detail hereinafter. An additional lumen 44 is included to shield the leads of the thermistor 38. Thermistor 38 is used to monitor blood temperature and also allows total cardiac output to be determined by way of thermodilution. As will be elaborated upon hereinafter, total cardiac output is one factor used in calculating myocardial oxygen consumption.

One of the other factors needed to determine myocardial oxygen consumption is the difference in oxygen content between the right atrium 46 and the pulmonary artery 22 (i.e. between atrial and mixed venous blood). This difference is measured via two oxygen sensors positioned along the length of PAC 20. Namely, a first oxygen sensor 48 is located at a distal end 32 of PAC 20, while second sensor 52 is located proximal to the first. Locating second sensor 52 approximately 30 centimeters or more from distal end 32 of PAC 20 is preferred. With PAC 20 properly positioned within a patient's heart, first sensor 48 is positioned for readings within pulmonary artery 22 and second sensor 52 is positioned for readings within right atrium 46. Ideally, second sensor 52 will be located about 3–4 centimeters above the tricuspid valve 54. Nonetheless, oxygen saturation can also be measured from the superior vena cava, upstream from the atrium. This is because measuring oxygen saturation in a superior vena cava (central venous blood) provides the same information as measuring atrial blood.

The sensors can measure blood oxygen content in any number of ways. For example, chemical sensors can be employed in making the measurements. Additionally, the sensors need not be located on the length of PAC 20, rather direct blood sampling may be used in making the necessary measurements. In the preferred embodiment, however, optical sensors 56 are employed. One suitable optical sensor is described in U.S. Pat. No. 4,684,245 to Goldring. The sensor described in the '245 patent includes a series of light emitting diodes ("LEDs") and a photodetector.

LEDs 58 are used to radiate infrared light into an adjacent blood sinus whereby the sensor's photodetector 62 can detect infrared absorption by the blood. The oxygen level in the blood can be determined from the level of infrared absorption. The optical sensors 56 are operatively coupled to microprocessor 42 for use in storing and processing the detected oxygen levels. The catheter includes additional lumina (64, 66) for housing the leads to optical sensors 48 and 52.

The present invention can employ any microprocessor 42 suitable for carrying out the algorithms described herein. The microprocessor can either be carried on-board PAC 20 or it can be a physically separate stand alone computer, such as a laptop. Microprocessor 42 is used in computing the oxygen consumption by the heart or myocardial $VO_2$ on the basis of the following equation:

$$VO_2 = Q_v(C_{at} - C_v) + Q_v F_s(C_a - C_{at}) \qquad \text{Eq. 1}$$

where, $Q_v$ = pulmonary artery blood flow or total cardiac output; this value is obtained from thermistor 38.

$C_{at}$ = Oxygen ($O_2$) content in atrial blood; this value is obtained from second oxygen sensor 52 located within the right atrium 46.

$Cv$ = Oxygen ($O_2$) content in the pulmonary artery blood; this value is obtained from first oxygen sensor 48 located within pulmonary artery 22.

$C_a$ = Oxygen ($O_2$) content in the coronary artery (arterial saturation); this value is obtained from a pulse oximeter, through a noninvasive and standard technique known to most Intensive Care Units and anyone skilled in the art;

$F_s$ = fraction of total blood flow going to the myocardium; this value is unknown for any particular patient, but it can safely be approximated to be between 0.05 and 10.

Figure 5:
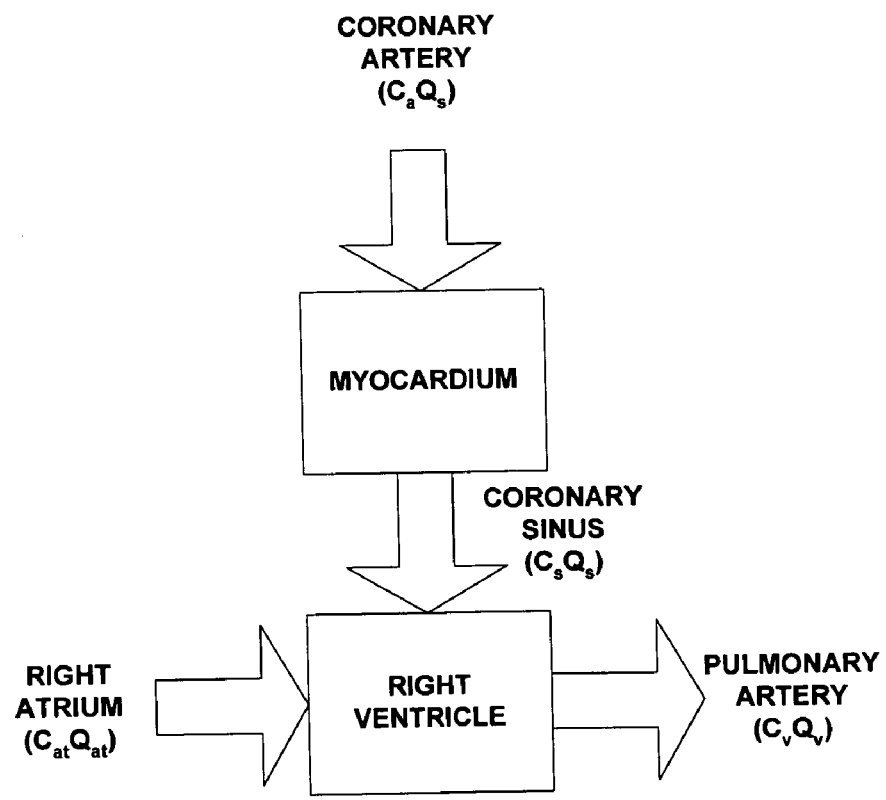
FIG. 5 is a block diagram illustrating blood flow and oxygen content from the coronary artery and right atrium into the pulmonary artery.

Equation 1 is derived from the principle of conservation of mass known as Fick's Principle as noted in the mass transport model depicted in FIG. 5 and the following equation:

$$VO_2 = C_a Q_s - C_s Q_s \qquad \text{Eq. 2}$$

The various $O_2$ contents referenced in Equation 1 are based on the well, known composition of $O_2$ within blood. That is, total $O_2$ is comprised of a percentage of $O_2$ bound to hemoglobin and a percentage of $O_2$ dissolved in plasma. The following equation reflects the known composition of $O_2$ within blood:

$$O_2 \text{ Content} = 1.34 \times \text{hemoglobin concentration} \times O_2 \text{saturation} + 0.0003 PO_2 \qquad \text{Eq. 3}$$

As can be observed from Equation 3, the percentage of $O_2$ from dissolved oxygen is quite small and can be neglected. In doing so, Equation 1 can be simplified as follows:

$$(VO_2) = KQ_v[(S_{at} - S_v) + F_s(S_a - S_{at})] \qquad \text{Eq. 4}$$

Here,
K=1.34×hemoglobin concentration.
$S_{at}$=Oxygen saturation in atrial blood.
$S_v$=Oxygen saturation in the pulmonary artery blood.
$S_a$=Arterial Oxygen saturation.

A close approximation to $VO_2$ is obtained by:

$$VO_2=K\,Q_v(S_{at}-S_v) \qquad \text{Eq. 5}$$

Microprocessor 42 can employ either Equations 1 or 4 in computing myocardial $VO_2$ consumption.

Figure 6:
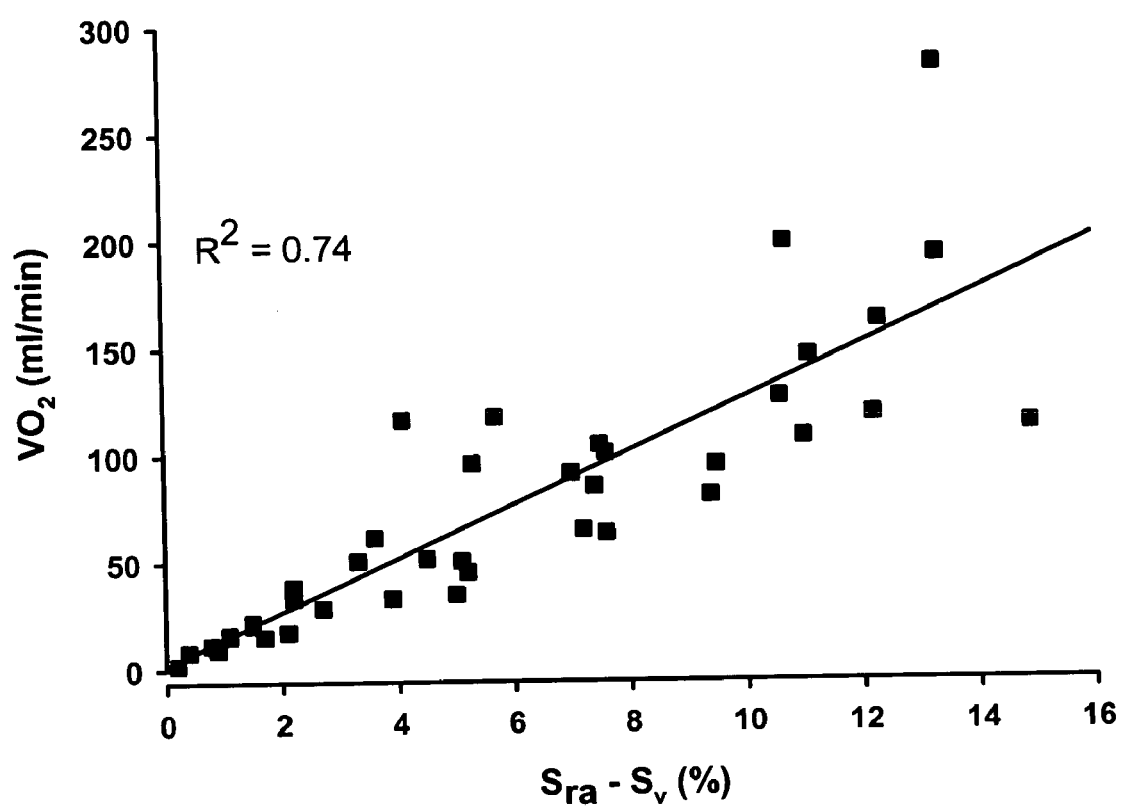
FIG. 6 is a graph illustrating the relationship between myocardial consumption and differential oxygen saturation between atrial and mixed venous blood.

FIG. 6 is a graph illustrating data taken from 50 patients in whom a single determination of $VO_2$ was made. FIG. 6 is a graph showing the [same data but shows] $VO_2$ plotted as a function of the difference in $O_2$ saturation between the first and second oxygen sensors. $VO_2$ was calculated using Equation 4 with Fs=0.05.

FIG. 6 illustrates that $VO_2$ is proportional to the difference in the saturation between the proximal and distal oxygen sensors. Therefore, the difference in $O_2$ saturation between atrial and mixed venous blood ($S_{at}-S_v$) could be used to monitor relative changes in $VO_2$ in a given patient without the need to measure Qv or hemoglobin saturation. It is also possible to monitor changes in $VO_2$ continuously by use of infrared optics placed in the tip and the atrial region of the PAC.

The principles presented herein can also be used to measure atrial and mixed venous blood differences in lactate, glucose and any other measurable blood concentration metabolite to serve as a measure of myocardial metabolism.

This is because the healthy myocardium generates its energy supply from the oxidation of fatty acids with the balance of energy production derived from the oxidation of glucose and lactate. Under aerobic conditions there is net lactate extraction from the coronary circulation with the oxidation of lactate accounting for 10% to 20% of the myocardial energy production, a proportion that increases substantially in septic patients. Given the heart's penchant for lactate as a metabolic substrate, coronary venous blood lactate concentration usually is lower than central venous blood lactate concentrate. The mixing of these effluents in the right ventricle should result in a declining blood lactate concentrate gradient from right atrium to pulmonary artery.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
What is claimed is:

1. A pulmonary artery catheter adapted to be inserted into a patient's venous system to detect the rate of oxygen consumption in the heart by comparing oxygen levels in the pulmonary artery to oxygen levels in the right atrium, or superior vena cava, the catheter comprising:
   an elongated flexible tube having an inflatable balloon at a distal end, a syringe positioned at a proximal end of the tube, the syringe allowing an operator to selectively inflate the balloon to thereby allow the catheter to be pulled through the patient's venous system;
   a thermistor proximal to the balloon, the thermistor measuring blood temperatures and determining cardiac output;
   a first oxygen sensor located adjacent the distal end of the tube and comprising a series of light emitting diodes and a photodetector, the first oxygen sensor determining blood oxygen content by measuring the blood's absorption of infrared light, the first oxygen sensor adapted to be positioned within a patient's pulmonary artery;
   a second oxygen sensor positioned proximal to the first oxygen sensor and likewise comprising a series of light emitting diodes and a photodetector, the second oxygen sensor determining blood oxygen content by measuring the blood's absorption of infrared light, the second oxygen sensor adapted to be positioned within a patient's right atrium or superior vena cava;
   a microprocessor operatively coupled to the first and second oxygen sensors, the microprocessor implementing an algorithm that calculates the rate of oxygen consumption in the heart as a function of the difference between blood oxygen content as measured by the first and second oxygen sensors and the cardiac output as determined by the thermistor.

2. A pulmonary artery catheter as described in claim 1 wherein the microprocessor carries out the following algorithm:

$$VO_2=KQ_v[(S_{at}-S_v)+F_s(S_a-S_{at})]$$

where,
K=1.34×hemoglobin concentration
$Q_v$=pulmonary artery blood flow or total cardiac output and is obtained from the thermistor;
$S_{at}$=Oxygen saturation in atrial blood is obtained from the second oxygen sensor;
$S_v$=Oxygen saturation in the pulmonary artery blood is obtained from the first oxygen sensor;
$S_a$=Arterial oxygen is obtained from a pulse oximeter;
$F_s$=fraction of total flow going to the myocardium and is approximated to be between 0.05 and 10.

3. A pulmonary artery catheter comprising:
   an elongated flexible tube;
   a first metabolite sensor located adjacent the distal end of the tube for determining blood metabolite content and adapted to be positioned within a patient's pulmonary artery;
   a second metabolite sensor positioned proximal to the first metabolite sensor and likewise determining blood metabolite content, the second metabolite sensor adapted to be positioned within a patient's right atrium or superior vena cava;
   a microprocessor operatively coupled to the first and second sensors, the microprocessor implementing an algorithm that calculates the rate of oxygen consumption in the heart as a function of the difference between blood metabolite content as measured by the first and second sensors.

4. The catheter as described in claim 3 wherein glucose is the metabolite measured by the first and second sensors.

5. A pulmonary artery catheter comprising:
   an elongated flexible tube;
   a first oxygen sensor located adjacent the distal end of the tube for determining blood oxygen content and adapted to be positioned within a patient's pulmonary artery;
   a second oxygen sensor positioned proximal to the first oxygen sensor and likewise determining blood oxygen content, the second oxygen sensor adapted to be positioned within a patient's right atrium or superior vena cava;

a microprocessor operatively coupled to the first and second oxygen sensors, the microprocessor implementing an algorithm that calculates the rate of oxygen consumption in the heart as a function of the difference between blood oxygen content as measured by the first and second oxygen sensors.

6. The pulmonary artery catheter as described in claim 5 wherein the first and second oxygen sensors are infrared sensors.

7. The pulmonary artery catheter as described in claim 5 wherein a thermistor is included at a distal end of the tube for measuring blood temperatures and determining cardiac output.

8. The pulmonary artery catheter as described in claim 5 wherein the tube includes an inflatable balloon at a distal end, a syringe positioned at a proximal end of the tube, the syringe allowing an operator to selectively inflate the balloon to thereby allow the catheter to be pulled through the patient's venous system.

9. The pulmonary artery catheter as described in claim 5 wherein the rate of oxygen consumption is calculated based on Fick's Principle.

10. A system for determining myocardial oxygen consumption of the heart comprising:
- a first oxygen sensor for determining blood oxygen content, the first sensor adapted to be positioned within the heart's pulmonary artery;
- a second oxygen sensor positioned proximal to the first oxygen sensor and likewise determining blood oxygen content, the second oxygen sensor adapted to be positioned within the heart's right atrium or superior vena cava;
- a microprocessor operatively coupled to the first and second oxygen sensors, the microprocessor implementing an algorithm that calculates the rate of oxygen consumption in the heart as a function of the difference between blood oxygen content as measured by the first and second oxygen sensors.

11. The system as described in claim 10 wherein the sensors are positioned on a catheter.

12. The system as described in claim 10 wherein the sensors are positioned on a pulmonary artery catheter.

* * * * *